(12) United States Patent
Shkurovich et al.

(10) Patent No.: US 8,321,018 B2
(45) Date of Patent: Nov. 27, 2012

(54) SYSTEMS AND METHODS FOR REDUCING OCCURRENCES OF ATRIAL ARRHYTHMIAS

(75) Inventors: Sergio Shkurovich, Encino, CA (US);
Anne M. Shelchuk, Cupertino, CA (US)

(73) Assignee: Pacesetter, Inc., Sylmar, CA (US)

( * ) Notice: Subject to any disclaimer, the term of this patent is extended or adjusted under 35 U.S.C. 154(b) by 80 days.

(21) Appl. No.: 13/027,174

(22) Filed: Feb. 14, 2011

(65) Prior Publication Data
US 2012/0209345 A1 Aug. 16, 2012

(51) Int. Cl.
*A61N 1/00* (2006.01)
(52) U.S. Cl. .......................................... 607/23
(58) Field of Classification Search ...................... 607/23
See application file for complete search history.

(56) References Cited

U.S. PATENT DOCUMENTS

| | | | |
|---|---|---|---|
| 4,425,920 A | 1/1984 | Bourland et al. | |
| 6,783,499 B2 | 8/2004 | Schwartz | |
| 6,970,742 B2 | 11/2005 | Mann et al. | |
| 7,363,081 B1 | 4/2008 | Kroll et al. | |
| 7,783,352 B1 | 8/2010 | Ryu et al. | |
| 2004/0255959 A1 | 12/2004 | Ducharme et al. | |
| 2006/0224201 A1* | 10/2006 | Hettrick et al. | 607/17 |
| 2010/0016735 A1 | 1/2010 | Harpas et al. | |
| 2010/0057155 A1 | 3/2010 | Farazi et al. | |

FOREIGN PATENT DOCUMENTS

| | | |
|---|---|---|
| WO | 2008039968 A2 | 4/2008 |
| WO | 2008039968 A3 | 6/2008 |

OTHER PUBLICATIONS

Israel, Carsten W., "The role of pacing mode in the development of atrial fibrillation," EUROPACE. 2006;8:89-95.

* cited by examiner

*Primary Examiner* — George Manuel

(57) ABSTRACT

A method for reducing occurrences of atrial arrhythmias includes obtaining measures indicative of atrial pressure of a patient, and monitoring for a change in the measures indicative of atrial pressure that is indicative of an increased vulnerability to an atrial arrhythmia. In response to detecting the change in the measures indicative of atrial pressure that is indicative of the increased vulnerability to an atrial arrhythmia, pacing therapy that is adapted to reduce atrial pressure and thereby reduce vulnerability to an atrial arrhythmia is selectively delivered. Additionally, or alternatively, pacing therapy is adjusted to reduce atrial pressure and thereby reduce vulnerability to an atrial arrhythmia.

19 Claims, 5 Drawing Sheets

SYSTEMS AND METHODS FOR REDUCING OCCURRENCES OF ATRIAL ARRHYTHMIAS

FIELD OF THE INVENTION

Embodiments of the present invention relate to implantable cardiac devices and methods for use therewith, that are used to reduce vulnerability to arrhythmias.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atriventricular bundle (AV bundle or His bundle) and then to the ventricles, which causes ventricular contraction. This sequence of events is known as sinus rhythm (SR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias; those that result in a faster heart rate than normal are called tachyarrhythmias. Tachyarrhythmias are further classified as supraventricular tachyarrhythmias (SVTs) and ventricular tachyarrhythmias (VTs). VTs are characterized by abnormally fast cardiac rhythms that originate in one of the ventricles. SVTs are characterized by abnormally fast cardiac rhythms that originate above the ventricles and may arise in the atria or the atrioventricular node (AV node). For example, a paroxysmal SVT can exhibit heart rates between approximately 140 beats per minute (bpm) and approximately 250 bpm. However, the most common SVTs are typically atrial flutter (AFl) and atrial fibrillation (AF). In addition, many SVTs involve the AV node, for example, AV nodal reentry tachycardia (AVNRT) where an electrical loop or circuit includes the AV node.

Atrial flutter (AFl) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, uncoordinated beats produce an arrhythmia known as atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the fast atrial activations. Hence, during AF, the ventricles may contract at a lesser rate than the atria, for example, of approximately 125 bpm to approximately 175 bpm.

Atrial arrhythmias are often caused by the presence of a viable substrate and the occurrence of triggers. A viable substrate includes the presence of dispersions of refractoriness and a slow conduction, and triggers can include ectopic beats. Typical techniques for managing atrial arrhythmias include curative approaches that seek to terminate arrhythmias once they have initiated. For example, atrial anti-tachycardia pacing (ATP) is used to terminate an episode of atrial tachyarrhythmia like AF. However, it would be desirable to avoid occurrences of atrial arrhythmias when possible.

SUMMARY

Embodiments of the present invention are related to implantable systems and methods for use therewith for reducing occurrences of atrial arrhythmias. In accordance with an embodiment, a method for reducing occurrences of atrial arrhythmias includes obtaining measures indicative of atrial pressure of a patient, and monitoring for a change in the measures indicative of atrial pressure that is indicative of an increased vulnerability to an atrial arrhythmia. In response to detecting the change in the measures indicative of atrial pressure that is indicative of the increased vulnerability to an atrial arrhythmia, pacing therapy that is adapted to reduce atrial pressure and thereby reduce vulnerability to an atrial arrhythmia is selectively delivered. Additionally, or alternatively, pacing therapy is adjusted to reduce atrial pressure and thereby reduce vulnerability to an atrial arrhythmia.

In an embodiment, monitoring for a change in the measures indicative of atrial pressure includes monitoring atrial stretch based on the measures indicative of atrial pressure of the patient and detecting the increase in vulnerability to an atrial arrhythmia when the monitored atrial stretch or the change in monitored atrial stretch exceeds a threshold.

In an embodiment, monitoring for a change in the measures in the measures indicative of atrial pressure that is indicative of an increased vulnerability to an atrial arrhythmia includes detecting the increased vulnerability to an atrial arrhythmia when one or more of the measures indicative of atrial pressure exceeds a corresponding threshold, or a change in the measures indicative of atrial pressure exceeds a corresponding threshold.

In an embodiment, selectively delivering pacing therapy that is adapted to reduce atrial pressure includes selectively delivering pacing to overdrive the sinus rate, which reduces blood volume in the atria, and thereby reduces vulnerability to an atrial arrhythmia by reducing atrial stretch.

In an embodiment, selectively delivering pacing therapy that is adapted to reduce atrial pressure includes adjusting at least one of atrio-ventricular (AV) delay and interventricular (VV) delay, to increase the filling time in the ventricles, which reduces blood in the atria by increasing a volume of blood being moved out of the atria, and thereby reduces vulnerability to an atrial arrhythmia by reducing atrial stretch.

In an embodiment, selectively delivering pacing therapy that is adapted to reduce atrial pressure includes adjusting timing between pacing at different locations within at least one of the ventricles during delivery of multisite ventricular pacing to increase the filling time in the ventricles. Increasing the filling time in the ventricles reduces blood in the atria by increasing a volume of blood being moved out of the atria, and thereby reduces vulnerability to an atrial arrhythmia by reducing atrial stretch.

In an embodiment, selectively delivering pacing therapy that is adapted to reduce atrial pressure includes selectively delivering atrial overdrive pacing to reduce occurrences of ectopic atrial activity that might initiate an atrial arrhythmia, and thereby reduces vulnerability to an atrial arrhythmia.

In accordance with an embodiment, once pacing therapy that is adapted to reduce atrial pressure is selectively initiated, the measures indicative of atrial pressure of the patient continue to be obtained and the pacing therapy that is adapted to reduce atrial pressure continues to be delivered until a further change in the measures indicative of atrial pressure is indicative of there no longer being an increased vulnerability to an atrial arrhythmia.

In accordance with an embodiment, once pacing therapy that is adapted to reduce atrial pressure is selectively initiated, the measures indicative of atrial pressure of the patient continue to be obtained and the measures indicative of atrial pressure are used as feedback to adjust pacing parameters associated with the pacing therapy and/or to switch to a different type of pacing therapy until a further change in the measures indicative of atrial pressure is indicative of there no longer being an increased vulnerability to an atrial arrhythmia.

The measures indicative of atrial pressure of the patient can be, but are not limited to, measures of left atrial pressure obtained from a pressure sensor implanted in the left atrium, measures of right atrial pressure obtained from a pressure sensor implanted in the right atrium, measures of pulmonary artery pressure that correlate with atrial pressure obtained from a pressure sensor implanted in the pulmonary artery, measures of right ventricular pressure that correlate with atrial pressure obtained from a pressure sensor implanted in the right ventricle, and/or measures of left ventricular pressure that correlate with atrial pressure obtained from a pressure sensor implanted in the left ventricle.

In accordance with an embodiment, a method for reducing occurrences of atrial arrhythmias includes obtaining measures indicative of atrial stretch of a patient, and monitoring for a change in the measures indicative of atrial stretch that is indicative of an increased vulnerability to an atrial arrhythmia. In response to detecting the change in the measures indicative of atrial stretch that is indicative of the increased vulnerability to an atrial arrhythmia, pacing therapy that is adapted to reduce atrial stretch and thereby reduce vulnerability to an atrial arrhythmia is selectively delivered. Additionally, or alternatively, pacing therapy to reduce atrial stretch and thereby reduce vulnerability to an atrial arrhythmia can be adjusted.

In an embodiment, obtaining measures indicative of atrial stretch of a patient includes obtaining measures indicative of atrial pressure of a patient, wherein the greater the measures indicative of atrial pressure the greater the atrial stretch. In this embodiment, monitoring for a change in the measures indicative of atrial stretch that is indicative of an increased vulnerability to an atrial arrhythmia includes detecting the increased vulnerability to an atrial arrhythmia when at least one of the obtained measures indicative of atrial pressure exceeds a threshold, or a change in the measures indicative of atrial stretch exceeds a threshold.

This summary is not intended to summarize all of the embodiments of the present invention. Further and alternative embodiments, and the features, aspects, and advantages of the embodiments of invention will become more apparent from the detailed description set forth below, the drawings and the claims.

DETAILED DESCRIPTION

Figure 1A:
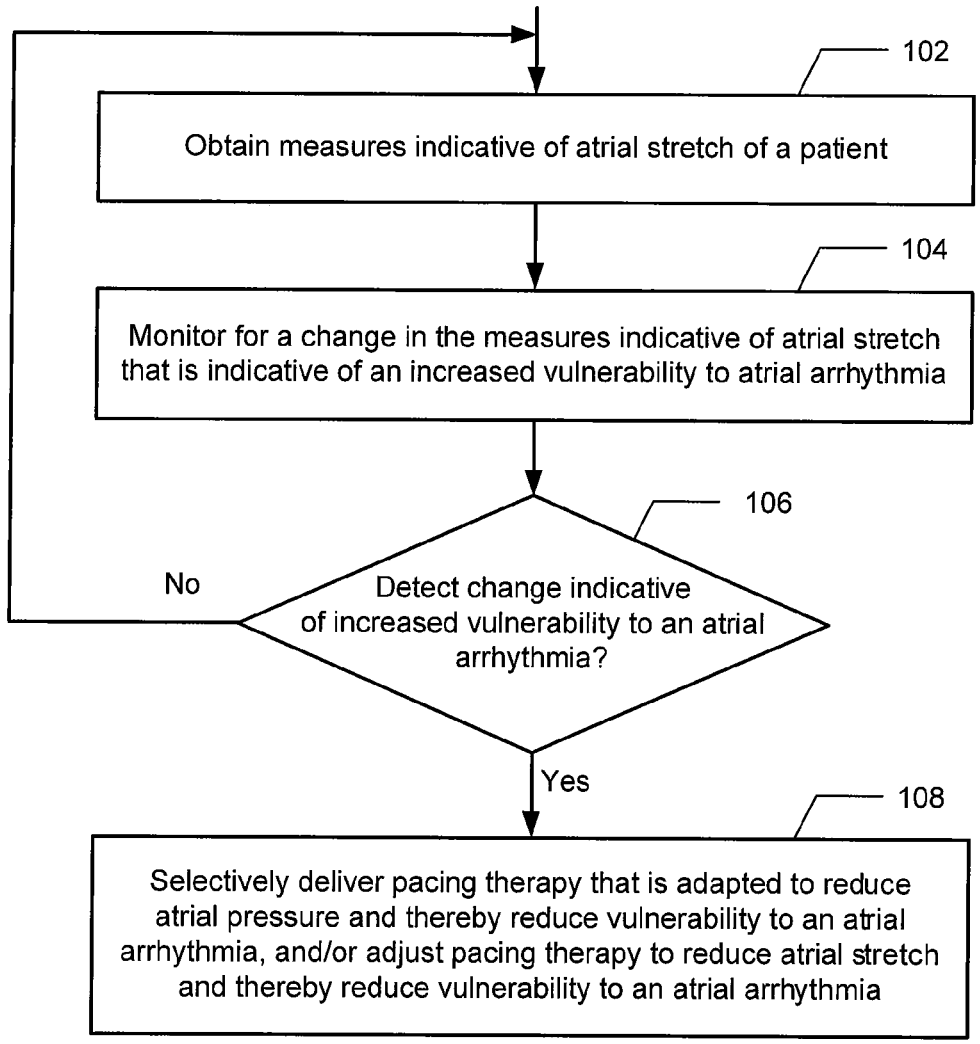
FIGS. 1A and 1B are high level flow diagrams that are used to summarize specific embodiments of the present invention that can be used to reduce vulnerability to an atrial arrhythmia.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

It has been observed that atrial stretch can be a factor for dispersion of refractoriness and is associated with the incidence of atrial arrhythmias such as atrial fibrillation (AF) and atrial flutter (AFI). For example, patients with AF have both the triggers necessary to start and the substrate to sustain their arrhythmia. The regions of the left atrium in and around the pulmonary veins are sources for both the initiators and the propagators of AF. The pulmonary veins are part of the arrhythmia substrate needed to allow AF to start and, once started, to continue. Factors that can cause the left atrium (and thus the attached pulmonary veins) to stretch can cause pulmonary vein initiators and propagators to form. Elevated left atrial pressure can result in atrial stretch, and thus can lead to dispersion of refractoriness that provides the necessary substrate for the maintenance of AF.

Certain embodiments that reduce occurrences of atrial arrhythmias monitor atrial stretch to identify periods in which an atrium may be more vulnerable to atrial arrhythmias and responsively apply and/or adjust therapy to prevent the occurrence of arrhythmias. Such therapy can be directed at reducing the substrate or suppressing the trigger. For example, increasing the ventricular rate to alleviate the accumulation of fluid in the left atrium can reduce atrial stretch. Alternatively, or additionally, applying pacing techniques such as atrial overdrive pacing suppression during periods of vulnerability can prevent the ectopic activity which can initiate the atrial arrhythmias given the substrate.

FIG. 1A is a high level flow diagram that is used to summarize various embodiments for reducing occurrences of atrial arrhythmias in a patient. Measures indicative of atrial stretch are obtained for the patient (Step 102) and the measures are monitored for a change indicative of an increased vulnerability to an atrial arrhythmia (Step 104). A measure indicative of atrial stretch can be a direct measurement of atrial stretch or an indirect measurement of atrial stretch. As mentioned above, an increase in atrial pressure can correlate to an increase in atrial stretch. Therefore, atrial pressure can be considered a surrogate indicative of atrial stretch. A measure indicative of atrial pressure (and therefore of atrial stretch) can be a direct measurement of atrial pressure or an indirect measure of atrial pressure. For example, in an embodiment, a measurement of left atrial pressure (LAP) can be obtained using a pressure sensor arranged within or exposed to the left atrium, while in an alternative embodiment, a measure of LAP can be indirectly obtained through measurement of left ventricular pressure (LVP) obtained at appropriate times during the cardiac cycle, for example, when the mitral valve opens. Any parameter that can be correlated with atrial stretch can be used as a measure indicative of atrial stretch.

The measures indicative of atrial stretch can be monitored for a change indicative of an increased vulnerability to an atrial arrhythmia, which change can be identified by a criterion or set of criteria. For example, in an embodiment the measure indicative of atrial stretch can be LAP, and the criterion can be a pressure threshold that, if exceeded, indicates a change indicative of an increased vulnerability to an atrial arrhythmia. In another embodiment a criterion can require that at least a predetermined number of measures exceed the threshold before the increased vulnerability is detected, that the measures exceed the threshold for at least a predetermined period of time, or that a running average of the measures exceeds the threshold, etc.

Any criterion or set of criteria can be prescribed by a physician indicating an increase in vulnerability that triggers a response and/or indicating a decrease in vulnerability that terminates the response. The criterion for detecting an increase in vulnerability and a decrease in vulnerability can be independent and can be different. For example, in an embodiment the measure indicative of atrial stretch that triggers a response can be LAP, and a set of criteria for indicating an increase in vulnerability to an atrial arrhythmia can include LAP exceeding a pressure threshold and/or a rate of increase in LAP exceeding a rate of increase threshold. A criterion for indicating a decrease in vulnerability to an atrial arrhythmia that terminates the response can be, for example, LAP below a pressure threshold for a specified period of time. One of ordinary skill in the art will appreciate the many different combinations of criteria can be applied to gate a status designation that an atrium has an increased vulnerability to an atrial arrhythmia.

In response to detecting the change in the measures indicative of atrial stretch that is indicative of the increased vulnerability to an atrial arrhythmia (Step 106), pacing therapy adapted to reduce atrial stretch is selectively delivered to thereby reduce vulnerability to an atrial arrhythmia, and/or pacing therapy is adjusted to reduce atrial stretch to thereby reduce vulnerability to an atrial arrhythmia (Step 108). Various different pacing therapies that can be selectively delivered to reduce atrial stretch are discussed below. Pacing parameters that can be adjusted can include, but are not limited to, pacing rate, atrio-ventricular (AV) delay, interventricular (VV) delay, and pacing locations used for multi-site left ventricular (MSLV) pacing.

In one embodiment, ventricular pacing schemes can be applied to reduce atrial stretch. For example, increasing the ventricular rate can circulate blood through the heart chambers more quickly, thereby reducing the volume of blood within the left atrium, thereby reducing the amount of stretch of the left atrial myocardium; analogous to the natural response in heart rate following a PVC plus compensatory pause. The ventricular rate can be increased for a predefined period of time in response to detecting the change in the measures indicative of atrial stretch that is indicative of the increased vulnerability to an atrial arrhythmia. Alternatively, the ventricular rate can be increased for as long a period as the status designation of the left atrium indicates that there is an increased vulnerability to an atrial arrhythmia.

Bi-ventricular pacing techniques allow pacing of the left and right ventricles. Further, latency between the left ventricle and right ventricle stimulation can be altered with an effort to reduce the volume of blood within the left atrium, and thereby reduce the amount of stretch of the left atrial myocardium. Where existing pacing therapy is adjusted, at least one of the AV delay and VV delay can be adjusted to increase the filling time in the ventricles, reducing blood in the atria. The filling time in the ventricles can be increased by lengthening the AV delay. Additionally, or alternatively, the filling time in the ventricles can be increased by adjusting timing between pacing at different locations within at least one of the ventricles (e.g., the left ventricle) during delivery of multisite ventricular pacing. Other pacing schemes can similarly be temporarily modified, e.g., by increasing, decreasing, or otherwise altering pacing rates, delays, and/or intensity.

In an alternative embodiment, atrial pacing schemes can be applied to suppress ectopic foci. For example, pacing the atria at a slightly increased rate can overdrive the cells of the atria including those irritable cells that could otherwise begin pacing independent (i.e., generate ectopic beats) and compete with the intrinsic rhythm, thereby creating triggers for an atrial arrhythmia. Such pacing is known as dynamic atrial overdrive (DAO) pacing. Commonly, DAO pacing can be programmed by a physician or clinician as a permanent pacing scheme for patient's suffering from AF. By contrast, in an embodiment of the present invention, the atrial rate can be selectively increased for a predefined period of time in response to detecting the change in the measures indicative of atrial stretch that is indicative of the increased vulnerability to an atrial arrhythmia. Alternatively, the atrial rate can be increased for as long a period as the status designation of the left atrium indicates an increased vulnerability to an atrial arrhythmia. The overdrive pacing rate can be fixed, e.g., a predetermined percentage (e.g., 10%) greater than the sinus rate, or in alternative embodiments the overdrive pacing rate can be gradually ramped up (but not past a predetermined maximum). Ramping can be performed in a predetermined manner, or in a responsive manner, e.g., ramping up can continue until the desired response is detected, e.g., when an acceptable decrease in vulnerability to an atrial arrhythmia is detected. When the desired response is detected, overdrive pacing can be terminated, or alternatively the overdrive pacing rate can be ramped back down.

In still other embodiments, synchronicity can be maintained by increasing both the ventricular rate and the atrial rate. In still other embodiments, the ventricular rate and the atrial rate can be increased by different degrees and/or for different intervals, e.g., intervals having different lengths and/or different (or no) overlap can be used.

In still other embodiments, various pacing schemes can be applied in prioritized sequence based on the measured response. For example, if the atrial pressure remains high for a pre-defined period of time following delivery of a first pacing scheme, an alternative pacing scheme having the same or alternative goal (e.g., reducing atrial blood volume and/or suppressing atrial ectopic foci) can be applied. In this sense, therapy can be applied using a feedback loop approach. Using the measures indicative of atrial stretch as feedback, pacing parameters can be adjusted and/or a different type of pacing therapy can be applied until a further change in the measures indicative of atrial pressure is indicative of an acceptable reduction in the vulnerability to an atrial arrhythmia.

While embodiments of methods of reducing occurrences of atrial arrhythmias in a patient have been described herein particularly with regard to the left atrium, in other embodiments such methods can be applied by obtaining measures indicative of atrial stretch in the right atrium. The left atrium is generally subjected to higher pressures than the right atrium, and therefore generally more susceptible to triggers of atrial arrhythmias. However, ectopic foci can also exist within the right atrium, which can provide an arrhythmia substrate. Accordingly, embodiments of the present invention are not intended to be limited to measures indicative of atrial pressure and/or atrial stretch in the left atrium.

Figure 1B:
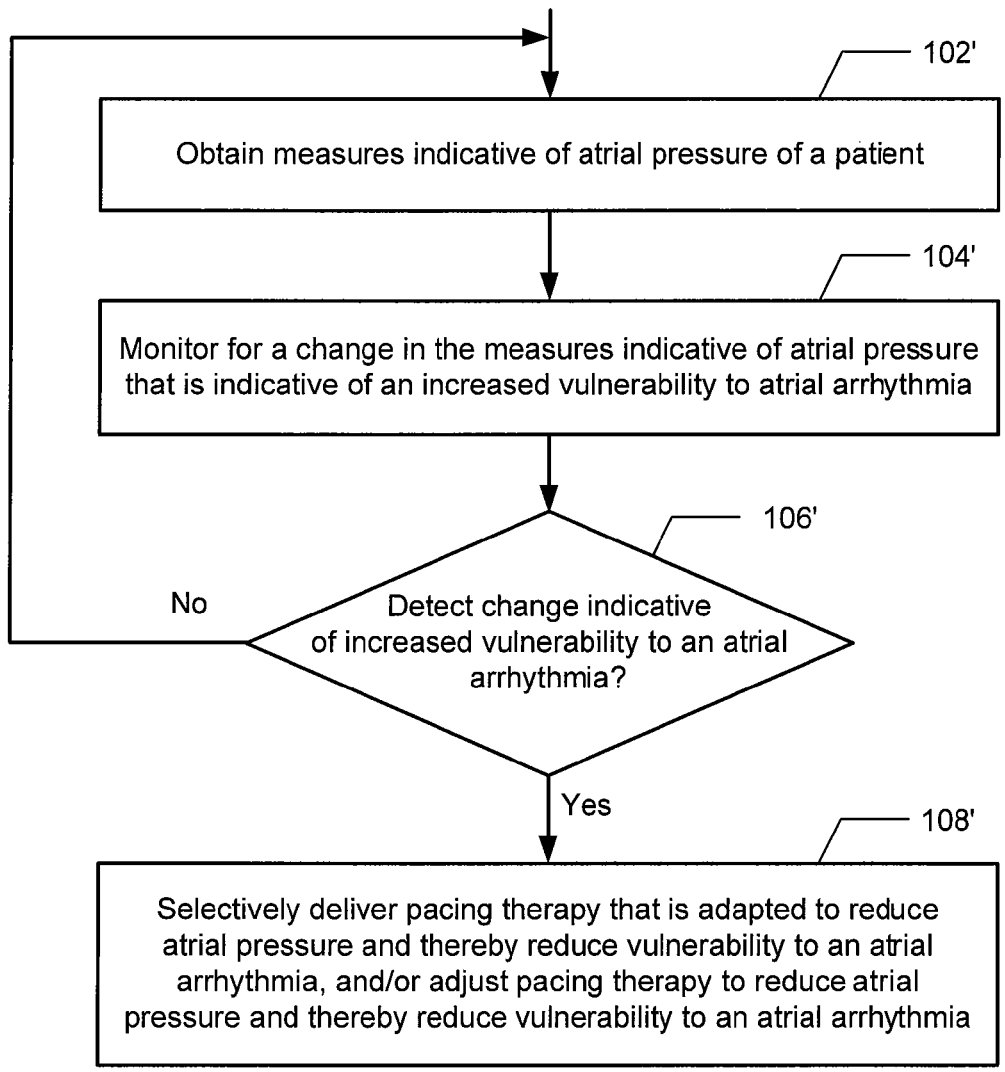

In an embodiment, explained with reference to the flow diagram of FIG. 1B, measures indicative of atrial pressure are used to monitor for an increased vulnerability to an atrial arrhythmia, with or without specifically also monitoring atrial stretch. Referring to FIG. 1B, measures indicative of atrial pressure of a patient are obtained (Step 102'). Exemplary techniques for obtaining such measures were described above, and are explained in additional detail below. The measures indicative of atrial pressure are monitored for a change that is indicative of an increased vulnerability to an atrial arrhythmia (Step 104'). In response to detecting the change in the measures indicative of atrial pressure that is indicative of the increased vulnerability to an atrial arrhythmia, pacing therapy that is adapted to reduce atrial pressure and thereby reduce vulnerability to an atrial arrhythmia is selectively delivered (Steps 106' and 108'). Additionally, or alternatively (at Step 108'), pacing therapy is adjusted to reduce atrial pressure and thereby reduce vulnerability to an atrial arrhythmia. Steps 102'-108' are similar to steps 102-108 described with reference to FIG. 1A, and one of ordinary skill in the art would understand how to perform steps 102'-108' based on the description of steps 102-108. Accordingly, steps 102'-108' need not be described in additional detail.

Embodiments of the present relate to methods for use by chronically implanted systems, as well as to chronically implanted systems, that determine (e.g., measure) metrics of atrial stretch to identify a vulnerability to an atrial arrhythmia, and to provide therapy to reduce the vulnerability to an atrial arrhythmia. An exemplary implantable cardiac system will thus be described in conjunction with FIGS. 2-4, in which embodiments of the present invention described herein could be implemented.

Exemplary Implantable System

Figure 2:
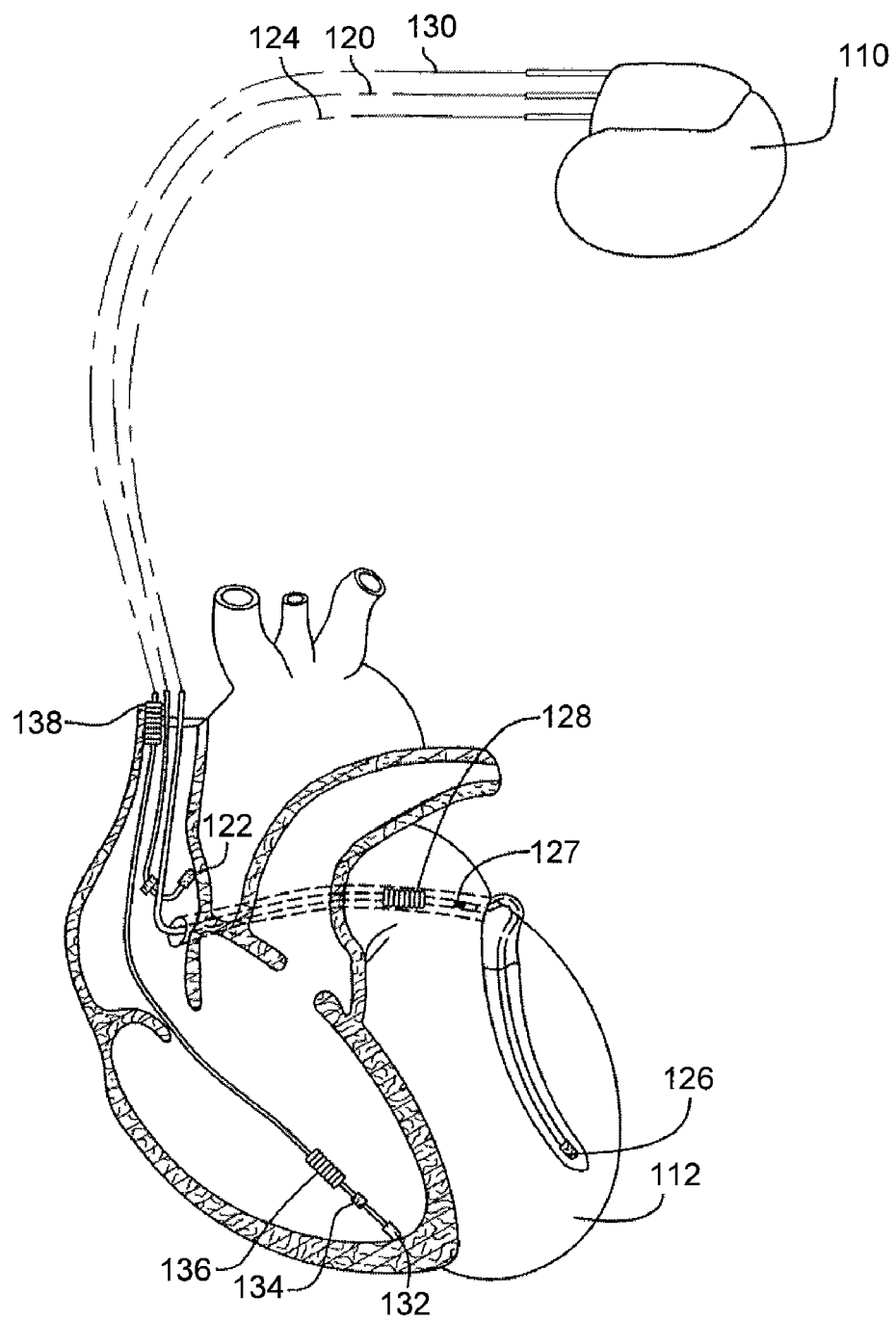
FIG. 2 is a simplified, partly cutaway view illustrating an implantable stimulation device in electrical communication with at least three leads implanted into a patient's heart for delivering multi-chamber stimulation and shock therapy and sensing cardiac activity.

Referring to FIG. 2, an exemplary chronically implantable device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. The device and the leads shall often be referred to hereafter collectively as a chronically implantable system. While not necessary to perform embodiments of the present invention, the exemplary device 110 is also capable of delivering shock therapy.

To sense atrial cardiac signals and to provide right atrial chamber stimulation, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention. More generally, electrodes may be positioned endocardially, epicardially or pericardially.

Figure 3:
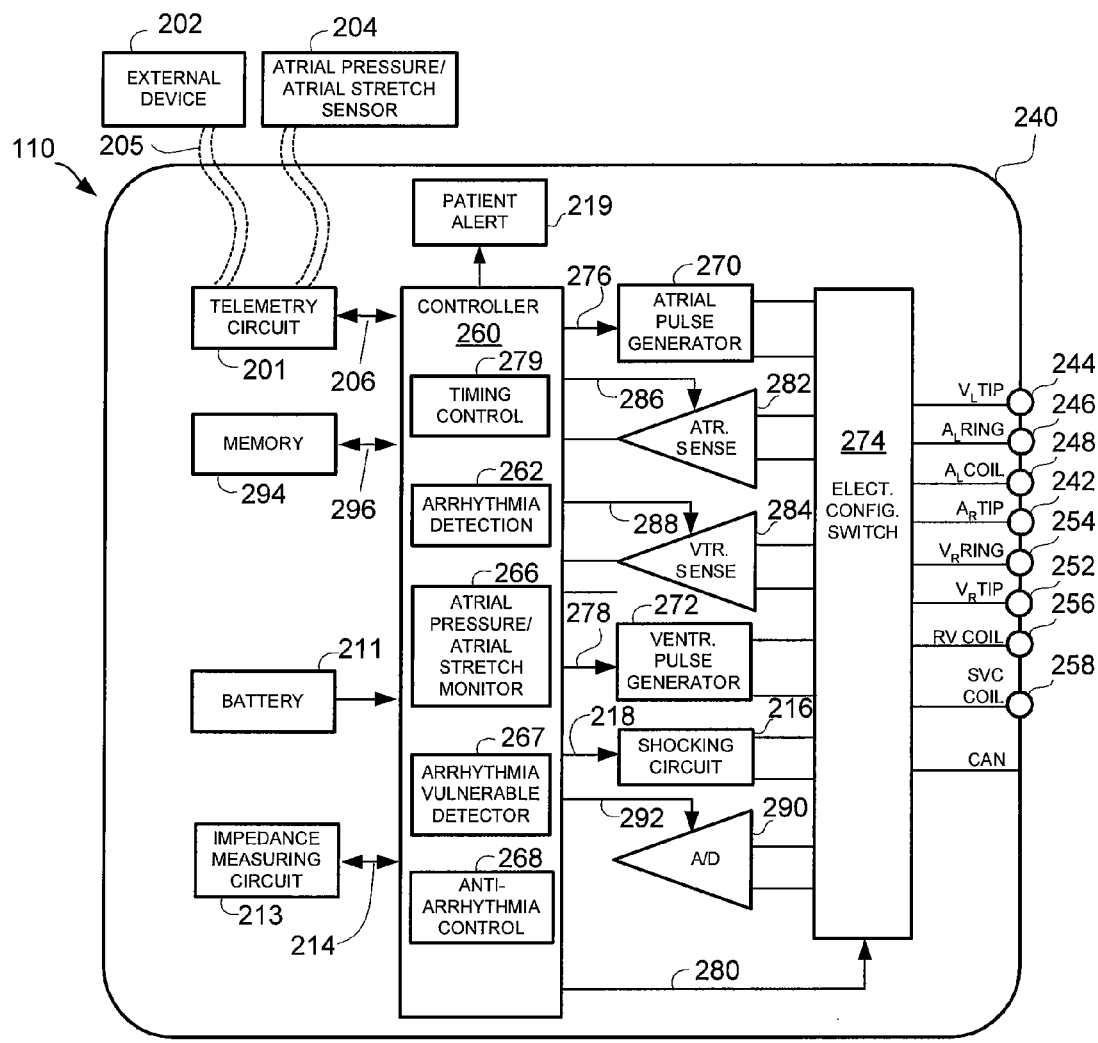
FIG. 3 is a functional block diagram of the multi-chamber implantable stimulation device of FIG. 2, illustrating the basic elements that provide pacing stimulation, cardioversion, and defibrillation in four chambers of the heart.

As illustrated in FIG. 3, a simplified block diagram is shown of the multi-chamber implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 3, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators 270, 272 may include dedicated, independent pulse generators, multiplexed pulse generators, or shared pulse generators. The pulse generators 270, 272 are controlled by the microcontroller 260 via appropriate control signals 276, 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial and ventricular sensing circuits 282, 284 may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit 282, 284 preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits 282, 284 can be used to determine cardiac performance values used in the present invention. Alternatively, an automatic sensitivity control circuit may be used to effectively deal with signals of varying amplitude.

The outputs of the atrial and ventricular sensing circuits 282, 284 are connected to the microcontroller 260 which, in turn, are able to trigger or inhibit the atrial and ventricular pulse generators 270, 272 respectively, in a demand fashion in response to the absence or presence of cardiac activity, in the appropriate chambers of the heart. The sensing circuits 282, 284 in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286. The sensing circuits can be used to acquire IEGM signals, which can be used to measure atrial evoked response metrics, in accordance with embodiments of the present invention.

For arrhythmia detection, the device 110 includes an arrhythmia detector 262 that utilizes the atrial and ventricular sensing circuits 282, 284 to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 3. Thus, this detector 262 can be implemented by software, firmware, or combinations thereof. It is also possible that all, or portions, of the arrhythmia detector 262 can be implemented using hardware. Further, it is also possible that all, or portions, of the arrhythmia detector 262 can be implemented separate from the microcontroller 260.

In accordance with embodiments of the present invention, the implantable device 110 also includes an atrial pressure/atrial stretch monitor 266, an arrhythmia vulnerability detector 267 and an anti-arrhythmia control 268. The atrial pressure/atrial stretch monitor 266 monitors a patient's atrial stretch and/or atrial pressure using embodiments of the present invention, which are described in detail above. The atrial pressure/atrial stretch monitor 266 can estimate atrial pressure and/or atrial stretch based on information received telemetrically or by way of one or more wires from an atrial pressure/atrial stretch sensor 204. In one embodiment, the atrial pressure/atrial stretch sensor 204 is a LAP sensor, and the atrial pressure/atrial stretch monitor correlates LAP with atrial stretch, or monitors LAP directly as a measure indicative of atrial stretch. The arrhythmia vulnerability detector 267 can monitor the measure(s) indicative of atrial pressure/atrial stretch for a change indicative of an increased vulnerability to an atrial arrhythmia in accordance with embodiments of the present invention described above. The anti-arrhythmia control 268 can select one or more responses to an increase in vulnerability to an atrial arrhythmia. The monitor 266, detector 267 and control 268 can be implemented by software, firmware, or combinations thereof. It is also possible that all, or portions, of monitor 266, detector 267 and control 268 can be implemented using hardware. Further, it is also possible that all, or portions, of the monitor 266, detector 267 and control 268 can be implemented separate from the microcontroller 260.

The implantable device can also include a patient alert 219, which produces a vibratory or auditory alert, or the like, when triggered.

Still referring to FIG. 3, cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also be used to store information related to methods for reducing occurrences of atrial arrhythmias. For example, the memory 294 can be used to store measures indicative of atrial stretch and/or atrial pressure obtained from the patient, and criteria related to status triggers.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. The telemetry circuit 201 can also be used to trigger alarms or alerts of the external device 202, or to instruct the external device 202 to notify a caregiver regarding detection of various episodes, occurrences and changes in conditions that are detected using embodiments of the present invention.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 3. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 3, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the implantable device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described implantable device 110 was described as an exemplary pacing device. One or ordinary skill in the art would understand that embodiments of the present invention can be used with alternative types of implantable devices. Accordingly, embodiments of the present invention should not be limited to use only with the above described device.

Figure 4:
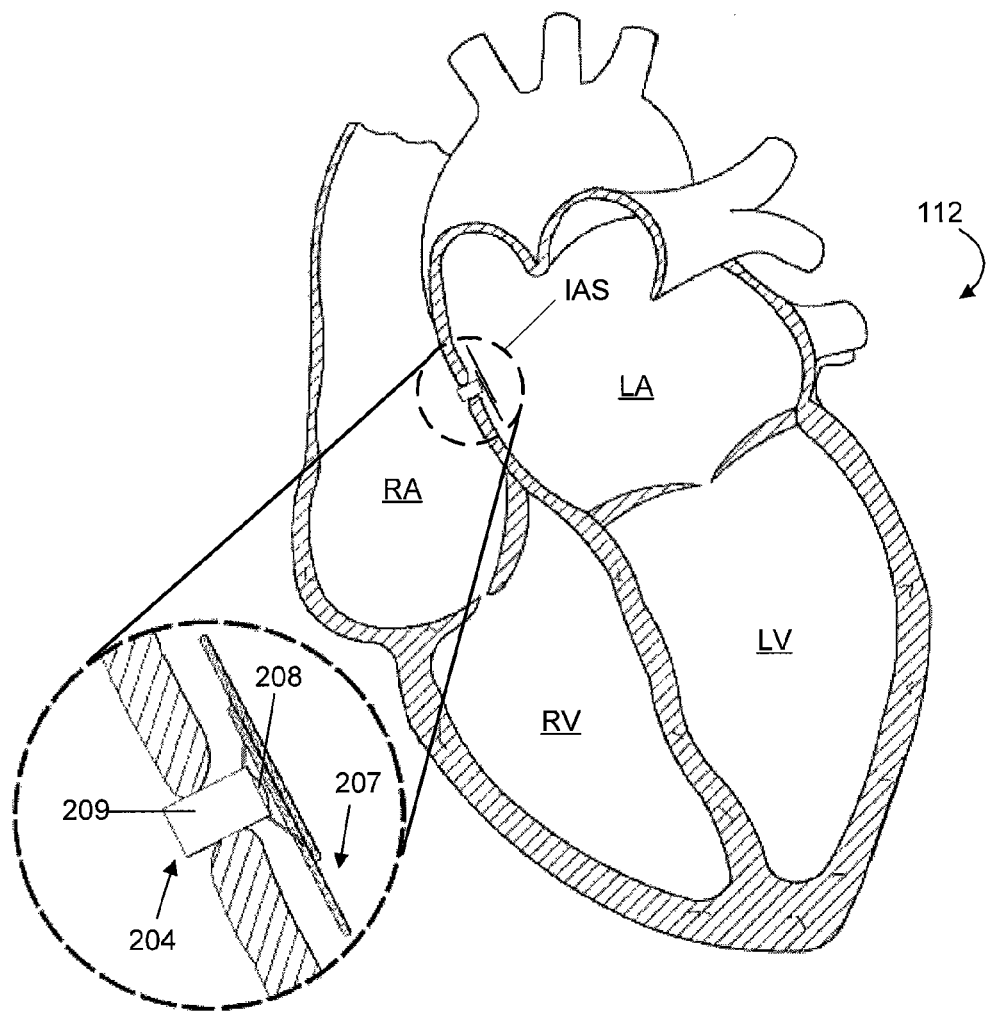
FIG. 4 is a simplified, cutaway view illustrating a pressure sensor positioned to measure left atrial pressure.

FIG. 4 illustrates an exemplary atrial pressure/atrial stretch sensor 204, which as shown is a pressure sensor, positioned to measure blood pressure within the left atrium LA of the heart 112. The left atrium LA can be accessed by trans-septal puncture of the intra-atrial septum (IAS) between the left atrium LA and the right atrium RA in order to implant the pressure sensor to measure pressure within the left atrium LA. The pressure sensor 204 can be implanted, for example, through the fossa ovalis. The pressure sensor 204 comprises a sensor housing 209, and a membrane 208 at one end of the sensor housing 209, wherein the membrane 208 is deformable in response to hemodynamic blood pressure. A microprocessor is positioned within the sensor housing 209 and operatively communicates with the membrane for transmitting a signal indicative of LAP. The pressure sensor 204 us also shown as including an antenna coil 207 which is operatively connected to the internal components of the sensor 204. The pressure sensor 204 can employ telemetry by way of the antenna coil 207 for transmitting or receiving data to/from the chronically implantable device 110 and/or an external device. Alternatively, the pressure sensor 204 can transmit or receive data to/from the chronically implantable device 110 by way of one or more wires.

As described above, in other embodiments the atrial pressure/atrial stretch sensor 204 can comprise a pressure sensor positioned in any of the other chambers of the heart (i.e. the left ventricle LV, right ventricle RV, and right atrium RA), or alternatively in a structure of the circulatory system well correlated with LAP, such as the pulmonary artery. The right atrium RA, for example, may be a preferred site for positioning a sensor because the sensor can be implanted almost anywhere in the right atrium RA. As described above, measurements obtained in the left ventricle LV, for example, may only be used during the appropriate point in the cardiac cycle when the LAP and left ventricle pressure LVP are substantially equalized (i.e. when the mitral valve is open). The pressure sensor need not be secured to the walls of the heart chamber. For example, the OPP-M pressure sensor from OPSENS® of Canada is positionable within the right atrium using a fiber optic cable. In still other embodiments, an atrial stretch sensor need not be a pressure sensor, but rather a sensor that detects some other metric or parameter directly or indirectly related to atrial stretch.

The present invention has been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 1A and 1B. Further, it is possible to change the order of some of the steps shown in FIGS. 1A and 1B, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable system, a method for reducing occurrences of atrial arrhythmias, the method comprising:
   (a) obtaining measures indicative of atrial pressure of a patient;
   (b) monitoring for a change in the measures indicative of atrial pressure that is indicative of an increased vulnerability to an atrial arrhythmia wherein monitoring comprises monitoring atrial stretch based on the measures indicative of atrial pressure of the patient and detecting the increased vulnerability to an atrial arrhythmia when the monitored atrial stretch exceeds a corresponding threshold, or a change in the monitored atrial stretch exceeds a corresponding threshold; and
   (c) in response to detecting the change in the measures indicative of atrial pressure that is indicative of the increased vulnerability to an atrial arrhythmia,
      selectively delivering pacing therapy that is adapted to reduce atrial pressure and thereby reduce vulnerability to an atrial arrhythmia, and/or
      adjusting pacing therapy to reduce atrial pressure and thereby reduce vulnerability to an atrial arrhythmia.

2. The method of claim 1, wherein detecting the increased vulnerability includes detecting that the monitored atrial stretch exceeds a corresponding threshold, or a change in the monitored atrial stretch exceeds a corresponding threshold, when one or more of the measures indicative of atrial pressure exceeds a corresponding threshold, or a change in the measures indicative of atrial pressure exceeds a corresponding threshold.

3. The method of claim 1, wherein step (b) includes detecting the increased vulnerability to an atrial arrhythmia when one or more of the measures indicative of atrial pressure exceeds a corresponding threshold, or a change in the measures indicative of atrial pressure exceeds a corresponding threshold.

4. The method of claim 1, wherein step (c) comprises selectively delivering pacing to overdrive the sinus rate, which reduces blood volume in the atria, and thereby reduces vulnerability to an atrial arrhythmia by reducing atrial stretch.

5. The method of claim 1, wherein step (c) comprises selectively delivering atrial overdrive pacing to reduce occurrences of ectopic atrial activity that might initiate an atrial arrhythmia, and thereby reduces vulnerability to an atrial arrhythmia.

6. The method of claim 1, further comprising:
   once pacing therapy that is adapted to reduce atrial pressure is selectively initiated;
   continue obtaining the measures indicative of atrial pressure of the patient; and
   continue delivering the pacing therapy that is adapted to reduce atrial pressure until a further change in the measures indicative of atrial pressure is indicative of there no longer being an increased vulnerability to an atrial arrhythmia.

7. The method of claim 1, further comprising:
once pacing therapy that is adapted to reduce atrial pressure is selectively initiated;
continue obtaining the measures indicative of atrial pressure of the patient while delivering the pacing therapy that is adapted to reduce atrial pressure; and
using the measures indicative of atrial pressure as feedback to adjust pacing parameters associated with the pacing therapy and/or to switch to a different type of pacing therapy until a further change in the measures indicative of atrial pressure is indicative of there no longer being an increased vulnerability to an atrial arrhythmia.

8. The method of claim 1, wherein the measures indicative of atrial pressure obtained at step (a) are selected from the group consisting of:
(a.1) measures of left atrial pressure obtained from a pressure sensor implanted in the left atrium;
(a.2) measures of right atrial pressure obtained from a pressure sensor implanted in the right atrium;
(a.3) measures of pulmonary artery pressure that correlate with atrial pressure obtained from a pressure sensor implanted in the pulmonary artery;
(a.4) measures of right ventricular pressure that correlate with atrial pressure obtained from a pressure sensor implanted in the right ventricle; and
(a.5) measures of left ventricular pressure that correlate with atrial pressure obtained from a pressure sensor implanted in the left ventricle.

9. For use with an implantable system, a method for reducing occurrences of atrial arrhythmias, the method comprising:
(a) obtaining measures indicative of atrial pressure of a patient;
(b) monitoring for a change in the measures indicative of atrial pressure that is indicative of an increased vulnerability to an atrial arrhythmia; and
(c) in response to detecting the change in the measures indicative of atrial pressure that is indicative of the increased vulnerability to an atrial arrhythmia,
selectively delivering pacing therapy that is adapted to reduce atrial pressure and thereby reduce vulnerability to an atrial arrhythmia, and/or
adjusting pacing therapy to reduce atrial pressure and thereby reduce vulnerability to an atrial arrhythmia;
wherein step (c) comprises adjusting at least one of atrio-ventricular (AV) delay and interventricular (VV) delay, to increase the filling time in the ventricles, which reduces blood in the atria by increasing a volume of blood being moved out of the atria, and thereby reduces vulnerability to an atrial arrhythmia by reducing atrial stretch.

10. For use with an implantable system, a method for reducing occurrences of atrial arrhythmias, the method comprising:
(a) obtaining measures indicative of atrial pressure of a patient;
(b) monitoring for a change in the measures indicative of atrial pressure that is indicative of an increased vulnerability to an atrial arrhythmia; and
(c) in response to detecting the change in the measures indicative of atrial pressure that is indicative of the increased vulnerability to an atrial arrhythmia,
selectively delivering pacing therapy that is adapted to reduce atrial pressure and thereby reduce vulnerability to an atrial arrhythmia, and/or
adjusting pacing therapy to reduce atrial pressure and thereby reduce vulnerability to an atrial arrhythmia;
wherein step (c) comprises adjusting timing between pacing at different locations within at least one of the ventricles during delivery of multisite ventricular pacing, to increase the filling time in the ventricles, which reduces blood in the atria by increasing a volume of blood being moved out of the atria, and thereby reduces vulnerability to an atrial arrhythmia by reducing atrial stretch.

11. For use with an implantable system, a method for reducing occurrences of atrial arrhythmias, the method comprising:
(a) obtaining measures indicative of atrial stretch of a patient;
(b) monitoring for a change in the measures indicative of atrial stretch that is indicative of an increased vulnerability to an atrial arrhythmia; and
(c) in response to detecting the change in the measures indicative of atrial stretch that is indicative of the increased vulnerability to an atrial arrhythmia,
selectively delivering pacing therapy that is adapted to reduce atrial stretch and thereby reduce vulnerability to an atrial arrhythmia, and/or
adjusting pacing therapy to reduce atrial stretch and thereby reduce vulnerability to an atrial arrhythmia.

12. The method of claim 11, wherein:
step (a) includes obtaining measures indicative of atrial pressure of a patient, wherein the greater the measures indicative of atrial pressure the greater the atrial stretch; and
step (b) includes detecting the increased vulnerability to an atrial arrhythmia when at least one of the obtained measures indicative of atrial pressure exceeds a threshold, or a change in the measures indicative of atrial stretch exceeds a threshold.

13. An implantable system for reducing occurrences of atrial arrhythmias, comprising:
a sensor configured to obtain measures indicative of atrial pressure of a patient;
a monitor configured to monitor for a change in the measures indicative of atrial pressure that is indicative of an increased vulnerability to an atrial arrhythmia, wherein the monitor is adapted to monitor atrial stretch based on the measures indicative of atrial pressure of the patient, and detect the increased vulnerability to an atrial arrhythmia when the monitored atrial stretch exceeds a corresponding threshold, or a change in the monitored atrial stretch exceeds a corresponding threshold; and
a controller configured to control pacing therapy;
wherein in response to the monitor detecting the change in the measures indicative of atrial pressure that is indicative of an increased vulnerability to an atrial arrhythmia, the controller is configured to
selectively deliver pacing therapy that is adapted to reduce atrial pressure and thereby reduce vulnerability to an atrial arrhythmia, and/or
adjust pacing therapy to reduce atrial pressure and thereby reduce vulnerability to an atrial arrhythmia.

14. The system of claim 13, wherein the sensor is arrangeable at a site selected from the group consisting of:
the left atrium to obtain measures of left atrial pressure;
the right atrium to obtain measures of right atrial pressure;
the pulmonary artery to obtain measures of pulmonary artery pressure that correlate with atrial pressure;
the right ventricle to obtain measures of right ventricular pressure that correlate with atrial pressure; and
the left ventricle to obtain measures of left ventricular pressure that correlate with atrial pressure.

15. An implantable system for reducing occurrences of atrial arrhythmias, comprising:
- a sensor configured to obtain measures indicative of atrial pressure of a patient;
- a monitor configured to monitor for a change in the measures indicative of atrial pressure that is indicative of an increased vulnerability to an atrial arrhythmia; and
- a controller configured to control pacing therapy;
- wherein in response to the monitor detecting the change in the measures indicative of atrial pressure that is indicative of an increased vulnerability to an atrial arrhythmia, the controller is configured to selectively deliver pacing therapy that is adapted to reduce atrial pressure and thereby reduce vulnerability to an atrial arrhythmia, and/or adjust pacing therapy to reduce atrial pressure and thereby reduce vulnerability to an atrial arrhythmia;
- wherein in response to the monitor detecting the change in the measures indicative of atrial pressure that is indicative of an increased vulnerability to an atrial arrhythmia, the controller is configured to:
- selectively deliver pacing to overdrive the sinus rate, which reduces blood volume in the atria, and thereby reduces vulnerability to an atrial arrhythmia by reducing atrial stretch;
- adjust at least one of atrio-ventricular (AV) delay and inter-ventricular (VV) delay, to increase the filling time in the ventricles, which reduces blood in the atria by increasing a volume of blood being moved out of the atria, and thereby reduces vulnerability to an atrial arrhythmia by reducing atrial stretch;
- adjust timing between pacing at different locations within at least one of the ventricles during delivery of multisite ventricular pacing, to increase the filling time in the ventricles, which reduces blood in the atria by increasing a volume of blood being moved out of the atria, and thereby reduces vulnerability to an atrial arrhythmia by reducing atrial stretch; and/or
- selectively deliver atrial overdrive pacing to reduce occurrences of ectopic atrial activity that might initiate an atrial arrhythmia, and thereby reduces vulnerability to an atrial arrhythmia.

16. An implantable system for reducing occurrences of atrial arrhythmias, comprising:
- a sensor configured to obtain measures indicative of atrial stretch of a patient;
- a monitor configured to monitor for a change in the measures indicative of atrial stretch that is indicative of an increased vulnerability to an atrial arrhythmia; and
- a controller configured to control pacing therapy;
- wherein in response to the monitor detecting the change in the measures indicative of atrial stretch that is indicative of an increased vulnerability to an atrial arrhythmia, the controller is configured to selectively deliver pacing therapy that is adapted to reduce atrial pressure and thereby reduce vulnerability to an atrial arrhythmia, and/or adjust pacing therapy to reduce atrial pressure and thereby reduce vulnerability to an atrial arrhythmia.

17. The system of claim 16, wherein:
- the measures indicative of atrial stretch include measures indicative of atrial pressure of a patient, wherein the greater the measures indicative of atrial pressure the greater the atrial stretch; and
- the monitor is configured to detect the increased vulnerability to an atrial arrhythmia when at least one of the obtained measures indicative of atrial pressure exceeds a threshold, or a change in the measures indicative of atrial stretch exceeds a threshold.

18. The system of claim 16, wherein the sensor is a pressure sensor arrangeable at a site selected from the group consisting of:
- the left atrium to obtain measures of left atrial pressure;
- the right atrium to obtain measures of right atrial pressure;
- the pulmonary artery to obtain measures of pulmonary artery pressure that correlate with atrial pressure;
- the right ventricle to obtain measures of right ventricular pressure that correlate with atrial pressure; and
- the left ventricle to obtain measures of left ventricular pressure that correlate with atrial pressure.

19. The system of claim 16, wherein in response to the monitor detecting the change in the measures indicative of atrial stretch that is indicative of an increased vulnerability to an atrial arrhythmia, the controller is configured to:
- selectively deliver pacing to overdrive the sinus rate, which reduces blood volume in the atria, and thereby reduces vulnerability to an atrial arrhythmia by reducing atrial stretch;
- adjust at least one of atrio-ventricular (AV) delay and inter-ventricular (VV) delay, to increase the filling time in the ventricles, which reduces blood in the atria by increasing a volume of blood being moved out of the atria, and thereby reduces vulnerability to an atrial arrhythmia by reducing atrial stretch;
- adjust timing between pacing at different locations within at least one of the ventricles during delivery of multisite ventricular pacing, to increase the filling time in the ventricles, which reduces blood in the atria by increasing a volume of blood being moved out of the atria, and thereby reduces vulnerability to an atrial arrhythmia by reducing atrial stretch; and/or
- selectively deliver atrial overdrive pacing to reduce occurrences of ectopic atrial activity that might initiate an atrial arrhythmia, and thereby reduces vulnerability to an atrial arrhythmia.

* * * * *